United States Patent [19]
Patnaik et al.

[11] Patent Number: 6,107,416
[45] Date of Patent: *Aug. 22, 2000

[54] POLYMER COATINGS GRAFTED WITH POLYETHYLENE OXIDE CHAINS CONTAINING COVALENTLY BONDED BIO-ACTIVE AGENTS

[75] Inventors: Birendra K. Patnaik, Chester, N.J.; Richard J. Zdrahala, So. Bloomington, Minn.

[73] Assignee: Scimed Life Systems, Inc., Maple Grove, Minn.

[*] Notice: This patent is subject to a terminal disclaimer.

[21] Appl. No.: 09/243,378

[22] Filed: Feb. 1, 1999

Related U.S. Application Data

[63] Continuation of application No. 08/755,189, Nov. 25, 1996, Pat. No. 5,877,263.

[51] Int. Cl.$^7$ .................................................. C08G 18/30
[52] U.S. Cl. ............................ 525/453; 525/460; 528/76; 427/2.1; 523/112
[58] Field of Search ..................... 525/453, 460; 528/76; 427/2.1; 523/112

[56] References Cited

U.S. PATENT DOCUMENTS

| | | | |
|---|---|---|---|
| 4,229,838 | 10/1980 | Mano | 427/2 |
| 4,331,697 | 5/1982 | Kudo et al. | 427/2 |
| 4,521,564 | 6/1985 | Solomon et al. | 428/423.3 |
| 4,600,652 | 7/1986 | Solomon et al. | 525/54.1 |
| 4,613,517 | 9/1986 | Williams et al. | 427/2 |
| 4,642,242 | 2/1987 | Solomon et al. | 427/2 |
| 4,678,660 | 7/1987 | McGary et al. | 424/25 |
| 4,713,402 | 12/1987 | Solomon | 523/112 |
| 4,720,512 | 1/1988 | Hu et al. | 523/112 |
| 4,786,556 | 11/1988 | Hu et al. | 428/412 |
| 4,973,493 | 11/1990 | Guire | 427/2 |
| 4,979,959 | 12/1990 | Guire | 623/66 |
| 5,028,597 | 7/1991 | Kodama et al. | 514/56 |
| 5,061,777 | 10/1991 | Yoda et al. | 528/61 |
| 5,077,352 | 12/1991 | Elton | 525/409 |
| 5,077,372 | 12/1991 | Hu et al. | 528/70 |
| 5,132,108 | 7/1992 | Narayanan et al. | 424/422 |
| 5,134,192 | 7/1992 | Feijen et al. | 525/54.1 |
| 5,171,264 | 12/1992 | Merrill | 427/2 |
| 5,244,654 | 9/1993 | Narayanan | 424/422 |
| 5,258,041 | 11/1993 | Guire et al. | 623/66 |
| 5,409,696 | 4/1995 | Narayanan et al. | 424/422 |
| 5,436,291 | 7/1995 | Levy et al. | 524/706 |
| 5,451,424 | 9/1995 | Solomon et al. | 604/265 |
| 5,728,751 | 3/1998 | Patnaik | 523/112 |
| 5,741,881 | 4/1998 | Patnaik | 528/75 |
| 5,855,618 | 1/1999 | Patnaik | 623/11 |
| 5,877,263 | 3/1999 | Patnaik | 525/453 |

FOREIGN PATENT DOCUMENTS

| | | |
|---|---|---|
| 0 263 184 A1 | 4/1988 | European Pat. Off. |
| WO 89/05616 | 6/1989 | WIPO |
| WO 90/00343 | 1/1990 | WIPO |
| WO 91/19521 | 12/1991 | WIPO |

OTHER PUBLICATIONS

Heparin Immobilization Onto Segmented Polyurethaneurea Surfaces–Effect of Hydrophilic Spacers, by Ki Dong Park, Teruo Okano, Chisato Nojiri, and Sung Wan Kim, Journal of Biodmedical Materials Research, vol. 22, 977–992 (1988).

SPUU–PEO–Heparin Graft Copolymer Surfaces: Patentcy and Platelet Deposition in Canine Small Diameter Arterial Grafts by Won Gon Kim Ki Dong Park, Syed F. Mohammad and Sung Wan Kim; ASAIO Trans 37: M148–M149 (1991).

Synthesis and Characterization of SPUU–PEO–Heparin Graft Copolymers, by Ki Dong Park, Al Zhi Piao, Harvey Jacobs, Teruo Okano and Sung Wan Kim, Journal of Polymer Science: Part A: Polymer Chemistry; vol. 29, 1725–1737 (1991).

PEO–Modified Surfaces–In Vitro, Ex Vivo, and In Vivo Blood Compatibility by Ki Dong Park and Sung Wan Kim in Poly(Ethylene Glycol) Chemistry: Biotechnical and Biomedical Applications, 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi and Sung Wan Kim; ASAIO Trans 36: M168–M172 (1990).

Heparin Immobilization by Surface Amplification, Ai–Zhi Piao, Harvey A. Jacobs, Ki Dong Park, and Sung Wan Kim, ASAIO Journal 1992, Slide Forum 26, Biomaterials/Surface Treatments, pp. M638–M643.

*Primary Examiner*—Rachel Gorr
*Attorney, Agent, or Firm*—Hoffmann & Baron, LLP

[57] ABSTRACT

Disclosed are bio-active coating compositions for polymeric substrates. In particular, a bio-active coating is described which is the reaction product formed by providing a polymer backbone with at least one free isocyanate group, wherein the isocyanate group is pendant from the polymer backbone. There is further provided a hydrophilic, amine-terminated spacer which has at least one amine group at its first and second ends. One of the amine groups of the spacer is reacted with one or more of the isocyanate groups on the polymer backbone in the presence of an optional catalyst agent. A bio-active agent is then covalently bonded onto an unreacted end of the spacer in the presence of a catalyst. Also disclosed are coating compositions for a substrate and methods of preparing same.

11 Claims, No Drawings

POLYMER COATINGS GRAFTED WITH POLYETHYLENE OXIDE CHAINS CONTAINING COVALENTLY BONDED BIO-ACTIVE AGENTS

CROSS-REFERENCE TO RELATED APPLICATION

The present application is a continuation of co-owned U.S. Ser. No. 08/755,189, filed Nov. 25, 1996, now U.S. Pat. No. 5,877,263, which is hereby incorporated by reference.

FIELD OF INVENTION

The present invention relates generally to bio-active polymer coatings. More particularly, the present invention relates to an improved process for preparing polymer coatings that are attached to hydrophilic spacer groups which are covalently bonded to bio-active agents.

BACKGROUND OF THE INVENTION

It is well known to use bio-active materials to coat structures to be introduced into a living system. Over the last 30 years, research into this area has become increasingly important with the development of various bio-compatible substrates for use in contact with blood, such as, for example, vascular grafts, artificial organs, endoscopes, cannulas, and the like.

While various materials have been used to make such substrates, synthetic polymers have been increasingly popular as the preferred materials due to their anti-thrombogenic and good mechanical properties. For example, polyurethane is a useful and effective material with a variety of clinical applications. Although synthetic polymers, such as PTFE and polyurethane, are less thrombogenic than earlier materials, thrombus formation is still a problem. A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. Thus, thrombus formation is a serious complication in surgery and clinical application of artificial organs.

Various anti-thrombogenic agents, such as, heparin, have been developed and incorporated into bio-compatible substrates to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for substrates to be implanted into a host organism. Bacterial, viral and other forms of infection may lead to life-threatening complications when a substrate is implanted into a host organism. Thus, binding of an anti-infection agent to a surface of an implantable substrate can reduce the risk of infection when a substrate is introduced into a host organism.

The art is replete with various procedures for grafting bio-active molecules onto polymer surfaces to prevent thrombus formation and/or infection. For example, biocompatible polymer surfaces have been described with various benefits including decreased thrombogenicity, increased abrasion-resistance and improved hydrophilic lubricious properties. Alternatively, preparing polymeric surfaces to receive bio-active agents by plasma treatment is also well known in the art.

Various polyurethane coatings to which bio-active agents are added have also been described. For example, bio-active agents directly bound to the polymer backbone of a polymer coating material are known. Also, polymer coatings are described that include either covalently or ionically binding bio-active agents to substrate surfaces. For example, photochemical reactions are described which covalently bind bio-active agents to substrate surfaces. Also, quarternary ammonium reagents are described which ionically bind a bio-active agent to a substrate. In polyurethane coatings, various spacer molecules that link bio-active agents to polymer substrates have been described by several studies. These studies indicate that bio-active agents, such as, for example, heparin bound to polymer coatings, retain more of their activity if they are tethered away from the surface of an substrate by a spacer.

Various substrate surfaces have previously been described that are suitable for introducing into a biological system. For example, Yoda et al. in U.S. Pat. No. 5,061,777 disclose that polyurethanes and polyurethaneureas containing both hydrophilic and hydrophobic polyether segments are more anti-thrombogenic than substrates produced from either a hydrophilic or a hydrophobic polyol exclusively. Similarly, Elton in U.S. Pat. No. 5,077,352 discloses a method of forming a mixture of an isocyanate, a polyol and a poly (ethylene oxide) in a carrier liquid. This mixture is then heated and cured to form a coating of a polyurethane complexed with a poly(ethylene oxide) having good adherence to a substrate and good anti-friction properties.

A significant limitation of these bio-compatible polymer surfaces, however, is that they are not completely biocompatible. Thrombus formation and infection continue to pose problems when a substrate is implanted within a host using these bio-compatible polymer surfaces. Thus, various alternative methods have been described for preparing the surface of a substrate to be implanted in a host organism to accept bio-active agents. Plasma treatment of substrate surfaces is one such method.

For example, Hu et al. in U.S. Pat. No. 4,720,512 disclose a method for imparting improved anti-thrombogenic activity to a polymeric support structure by coating it with an amine-rich material, e.g., a polyurethaneurea, introducing hydrophobic groups into the amine-rich surface coating through plasma treatment with fluorine compounds, and covalently bonding an anti-thrombogenic agent to the hydrophobic amine-rich surface.

Such a method for plasma treating a substrate surface is limited in its scope because it only works with certain substrates. Thus, it does not provide a general purpose coating composition that can bind to a variety of substrate surfaces. In an alternate approach, however, various methods have been described for binding bio-active agents directly to substrate surfaces.

For example, Solomon et al. in U.S. Pat. No. 4,642,242 disclose a process for imparting anti-thrombogenic activity to a polyurethane polymer material by coating a support structure with a protonated amine-rich polyurethaneurea, activating the amine moiety with an alkaline buffer, and covalently linking an anti-thrombogenic agent, e.g., heparin, to the polyurethaneurea with a reducing agent.

Bio-active agents bound directly to polymer backbones suffer from several limitations. First, because these bio-active agents are directly linked to the polymer backbone, their in vivo mobility is decreased. Second, the process of linking the bio-active agent to the polymer backbone may diminish the number of functional binding sites on the bio-active agent. Third, the bio-active agent's close proximity to the polymer backbone limits its ability to interact with its physiological substrates. Thus, for all of these reasons, coatings containing bio-active molecules bound directly to the polymer backbone are limited by the bio-active agent's decreased activity.

Accordingly, alternative methods have been developed for binding bio-active molecules to substrate surfaces. In particular, methods for ionically binding bio-active agents to a substrate via a quaternary ammonium compound have been described. See for example, Mano in U.S. Pat. No. 4,229,838, Williams et al. in U.S. Pat. No. 4,613,517, McGary et al. in U.S. Pat. No. 4,678,660, Solomon et al. in U.S. Pat. No. 4,713,402, and Solomon et al. in U.S. Pat. No. 5,451,424.

These methods, however, are severely limited because the bio-active agent is leached over time from the surface of the substrate. Thus, the protection afforded by the ionically bound bio-active agent to the substrate surface is transient at best. Accordingly, more permanent methods for binding bio-active molecules to substrate surfaces have also been developed. These methods include covalently binding a bio-active molecule, either directly, or via a spacer molecule, to a substrate surface.

For example, photochemical reactions have been described for preparing substrate surfaces to receive anti-thrombogenic agents. Kudo et al. in U.S. Pat. No. 4,331,697 disclose a method for imparting anti-thrombogenic activity to a biomedical material by directly linking a heparin derivative to the surface of the material via actinic radiation. Similarly, Kudo et al. also disclose coating a surface of a biomedical material with a polymer having a carboxylic acid halide group and/or a carboxylic anhydride functional group as a side chain that can react with a heparin derivative.

Alternatively, Guire et al. in U.S. Pat. Nos. 4,973,493 and 4,979,959 disclose methods for binding bio-active molecules to substrates using a linking moiety with functionalized end groups preferably that are activated by different signals. The linking moiety can covalently bind a bio-active molecule upon introduction of a first activation signal which activates the first functionalized end group. The linking moiety is further capable of covalently binding to the substrate upon introduction of a second, different, signal (photochemical) which activates the second functionalized end group.

Bichon et al. in U.S. Pat. No. 4,987,181 disclose a substrate having an adhesive film with anti-thrombogenic properties on its surface. This adhesive film is an olefinic copolymer having side groups distributed randomly on the main chain, wherein these side groups are carboxylic groups and groups of the formula —CONH—$(CH_2)_n$—$NH_2$—$CH_2$—R, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Although spacer molecules provide a means for optimizing the bio-activity of bio-agents bound to substrate surfaces, several problems persist in the photochemical reactions used to bind these bio-active molecules via spacers to substrate surfaces. Included among these problems are the ability of the bio-active molecule to withstand the photochemical signal used to bind it to the substrate surface, as well as, the ability of the substrate to withstand photoradiation. For example, inert polymeric substrates, e.g., polytetrafluoroethylene, degrade when exposed to photochemical reactions and cannot be used therewith. Thus, attempts have been made to use spacer molecules to bind bio-active agents to substrate surfaces without photochemical reactive groups.

For example, in a four step process, Park et al. disclose immobilizing heparin onto a commercial preparation of a segmented polyetherurethaneurea (PUU) using hydrophilic poly(ethylene oxide) (PEO) spacers of different molecular weights. Their method includes (1) coupling hexamethyldiisocyanate (HMDI) to a segmented polyetherurethaneurea backbone through an allophanate/biuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO complex. Next (3) the free hydroxyl groups of the PUU-PEO complex are treated with HMDI to introduce a terminal isocyanate group. Finally, (4) the NCO functionalized PUU-PEO is then covalently bonded to reactive functional groups on heparin (—OH and —$NH_2$) producing a PUU-PEO-Hep product. K. D. Park and S. W. Kim, "PEO-Modified Surfaces-In Vitro, Ex Vivo and In Vivo Blood Compatibility", in Poly(Ethylene Glycol) Chemistry: Biotechnical and Biomedical Applications 283 (J. Milton Harris ed. 1992). This method will be referred to hereinafter as the "Park Method."

The Park Method, however, suffers from several draw backs. In particular, because of the number of reactions steps involved in the Park Method, the synthesis of the coating composition is slow, inefficient and prone to side reactions which contributes to the low yield and an increase in the amount of cross-linked polymer.

In general, all of these disclosures have addressed substrate surfaces and/or coatings therefor which can exist within biological systems and in particular, can increase the anti-thrombogenicity of the surface of, e.g., medical substrates. These reactions, however, are generally slow, multi-step syntheses, and are characterized by side reactions which lead to low yields and formation of cross-linked polymers. In addition, these reactions cannot be universally applied to substrate surfaces. Thus, in particular, there is a need for a bio-active coating and process that can be used with a broad spectrum of substrate surfaces. In addition, there is a need particularly for a coating process that uses a hydrophilic amine-terminated spacer to maximize the bio-activity of the bio-active agent. There is also a need for a simplified bio-active coating process that provides a higher yield of polymer with negligible cross-linking in a shorter period of time. The present invention is directed toward providing a solution therefor.

SUMMARY OF THE INVENTION

The present invention relates to a bio-active coating formed by the process that includes providing a polymer backbone with at least one free reactive functionality which is pendant from the polymer backbone. There is further provided a hydrophilic spacer having at least one reactive functional group at its first and second ends. One of the reactive functional groups of the hydrophilic spacer is then reacted with one or more of the reactive functionalities on the polymer backbone. A bio-active agent is then covalently bonded onto the unreacted end of the spacer via the unreacted functional group to covalently bind the bio-active agent to the spacer.

In another embodiment of the present invention, a coating composition for a substrate is provided that includes a polymer backbone having a reactive functionality covalently bonded thereto and at least one pendant moiety bonded to the reactive functionality. The pendant moiety is selected from the group consisting of:

wherein $R^1$ is a spacer selected from the group consisting of aliphatic hydrocarbons, poly(oxy olefins), hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof.

In yet another embodiment of the present invention, there is provided a method for preparing a bio-active polymer coating having a bio-active group covalently bonded through a spacer group to a polymer backbone that includes introducing a reactive functionality into the polymer backbone; reacting the reactive functionality of the polymer backbone with a hydrophilic spacer having at least one reactive functional group at its terminal ends to attach the spacer as a pendant group off the backbone; and further reacting the pendant group with a bio-active agent to covalently bond the bio-active agent to the pendant group.

In a further embodiment of the present invention, there is provided a polymer-bound bio-active composition represented by the structure:

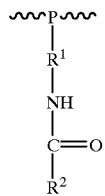

wherein P is a biocompatible polymer backbone having reactive functionality. The reactive functionality may be selected from the group consisting of isocyanates, carboxyls, amines and mixtures thereof. $R^1$ is a hydrophilic spacer group selected from the group consisting of aliphatic hydrocarbons, poly(oxy olefins), hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof.

In yet another embodiment, there is provided a bio-active coating having a polymer backbone and a bio-active agent bound thereto through a pendant hydrophilic spacer group. This bio-active coating is a reaction product that includes a polymer backbone having at least one free reactive pendant group, a hydrophilic spacer having at its first and second terminal ends at least one functional group which is reactive with the free reactive functional group, and a bio-active agent covalently reactive with an unreacted functional group in the hydrophilic spacer.

Thus, the invention provides a bio-active coating, coating compositions and a method for preparing same.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, novel bio-active coatings and their use in developing anti-thrombogenic and/or anti-infective substrates are provided. More particularly, new reaction schemes are provided for the synthesis of heparinized polyurethanes.

The bio-active coatings and method described herein are particularly advantageous over previously disclosed polymer coatings, especially the Park Method described herein above, because the composition and structure of the present coatings are more controllable and reproducible. In addition, the properties of the bio-active coatings of the present invention can be varied easily, e.g., biostability, hydrophilicity etc. Also, the methods of synthesizing the present bio-active coatings are more efficient and take less time than previously disclosed methods. Another advantage of the present invention is that the reactions may be carried out at lower temperatures. Importantly, the reaction schemes of the present invention form fewer cross-links and provide higher polymer yields than previously described methods.

The polymer backbones of the present invention are comb-type polymers in which bio-active molecules, such as heparin, are attached. Preferred polymers are siloxane-urethane copolymers, or most preferably, polyurethanes including poly(esterurethane)ureas, poly(etherurethane) ureas, poly(carbonateurethane)ureas, and mixtures thereof.

A bio-active coating composition of the invention was synthesized by a process that included reacting a segmented polyesterurethaneurea, such as for example, a commercially available preparation of BIOSPAN® (The Polymer Technology Group, Inc.; Emeryville, Calif.) with a polyol or a diisocyanate, such as for example, hexamethylene diisocyanate (HMDI). The resulting product was a poly (esterurethane)urea polymer containing isocyanate functionality (I). This polymer was then added to a hydrophilic spacer group, such as for example an amine-terminated poly(ethylene oxide) (II) in the presence of an optional catalyst, such as for example, 1-(3-dimethylaminopropyl)-3-ethylcarbodiimide hydrochloride (EDC) as indicated below:

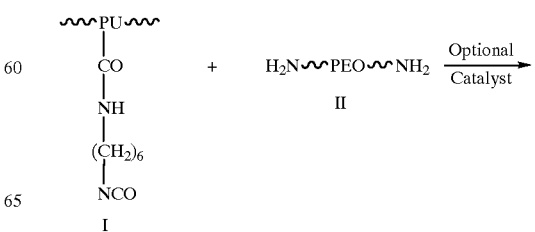

-continued

III

The product (III) of the reaction indicated above is a polymer-spacer complex. A bio-active agent, such as heparin, is then covalently bound to the polymer-spacer complex in the presence of a catalyst which may also function as a dehydrating agent in aqueous environments, such as, EDC, as indicated below:

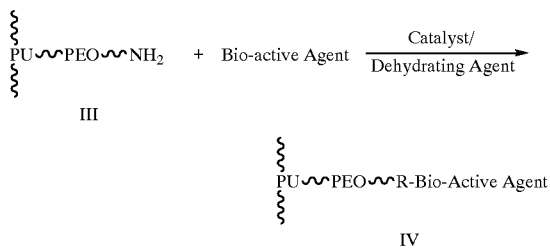

wherein R is selected from the group consisting of NHCO, NHCOO, and NHCONH. The product (IV) of the reaction indicated above is characterized by the presence of at least an amide linkage between the spacer and the bio-active molecule, e.g., heparin. This composition and its method of synthesis will be referred to hereinafter as "Inventive Embodiment I."

Thus, in Inventive Embodiment I, an optional catalyst is used to facilitate the reaction in which the spacer is covalently bound to the polyurethane backbone. Similarly, a catalyst is used to facilitate the reaction in which the bio-active agent is covalently bound to the polyurethane backbone via the hydrophilic spacer. Preferably, EDC catalyzes both of these reactions in the media of the present invention. In non-aqueous organic solvents, many carbodiimides can be used, such as, for example, dicyclohexyl carbodiimide.

As Table 1 indicates, the present invention, e.g., Inventive Embodiment I, significantly improves upon previously described bio-active coating compositions and methods of making same, such as the Park Method described herein.

TABLE 1

|  | Park Method | Inventive Embodiment I |
|---|---|---|
| Polymer Yield (gm/gm starting material) | 0.40 ± 0.5 | 0.70 ± 0.08 |
| Level of Polymer Cross-Linking (%) | Moderate (1–60) | Low (1–30) |
| Factor Xa Heparin Activity μg/cm$^2$ | 0.03 – 0.13 | 0.03 – 0.22 |

As illustrated in Table 1, the method of the present invention provides for approximately a 100% increase in polymer yield, while significantly decreasing the amount of polymer cross-inking, i.e. unwanted side-reactions and cross-reactions, and without sacrificing heparin bio-activity.

The bio-active agent of the present invention is bound to the polymer backbone via a spacer group. The spacer group may include aliphatic hydrocarbons, poly(oxy olefins), hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides. The spacer group is intended to be hydrophilic in order to take advantage of the natural repulsive forces of the hydrophobic substrate. The spacer group should have reactive functional groups on each end that are capable of reacting with, and binding to the polymer backbone and bio-active agent, respectively. Preferably, the reactive functional groups on each end of the spacer are, for example, NH$_2$ groups, COOH groups, NCO groups and mixtures thereof. An amino end-blocked poly(ethylene oxide) is a preferred example of such a spacer group.

Moreover, hydrophilic poly(ethylene oxide) spacers are preferred because they have low interfacial free energy, lack binding sites, and exhibit highly dynamic motion. These characteristics are important because they increase the activity of a PEO-linked bio-active agent, e.g., heparin. See, K. D. Park et al., supra.

As previously mentioned, the length of the spacer group may be used to control the bio-active agent's activity. It is known in the art that the anti-thrombogenic activity of heparin is increased when it is positioned a certain distance from the substrate to which it is bound. For example, in a comparison of polymer-spacer-heparin coatings using a C$_6$ alkyl spacer, PEO 200, PEO 1000 and PEO 4000, the polymer-PEO 4000-Heparin surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "effective distance" means the distance between the bound bio-active agent and the polymer backbone which corresponds to a desired level of activity in the bio-active agent.

Thus, in the present invention, control over the bio-active agent's activity is achieved by varying the length, i.e., molecular weight, of the spacer group. The spacer group may have a molecular weight of about 100 to about 200,000 daltons. Preferably, the spacer group has a molecular weight of about 200 to about 50,000 daltons. More preferably, the spacer group has a molecular weight of about 1,000 to about 10,000 daltons. Most preferably, the spacer group has a molecular weight of 4,000 daltons.

In accordance with the present invention, a significant reduction of thrombus formation and/or infection associated with the use of medical substrates is achieved by combining an anti-thrombogenic and/or an anti-infective agent in a coating to be applied to the host-contacting surface(s) of the substrate. A variety of anti-infective agents as known in the art may be used, including, antibiotics, such as penicillin and antibacterial agents such as silver sulfadiazine. Similarly, a variety of anti-thrombogenic agents known in the art may be used, including, heparin, aldehyde-terminated heparin, e.g., a nitrous acid degraded heparin molecule, hirudin, hirulog, prostaglandin, urokinase, streptokinase, sulfated polysaccharide, and albumin. In some cases it may be desirable to provide either dual anti-infective or anti-thrombogenicaction with two or more agents. Additionally, it may be desirable to combine an anti-infective and an anti-thrombogenic action by combining two or more of these different agents. The invention will be described in terms of the preferred heparin, a known anti-thrombogenic agent of known safety and high anti-coagulation activity, with the understanding that the invention contemplates any anti-thrombogenic and/or anti-infective agent which may be grafted to the polymer backbone by the method of the present invention.

A substrate of the invention may be any medical article compatible with a polymer bound bio-active agent coating which, absent the coating, may lead to thrombus formation and/or infection when in contact with a body tissue or fluid. Exemplary of, but not limited to, such substrates are vascular access (arterial and venous) catheters, introducers, vascular grafts, endoprosthesis, stents, stent-graft combinations, urinary catheters and associated substrates, such as drainage bags and connectors, and all abdominal cavity drainage tubing, bags and connectors. Preferred substrates are polymeric, such as for example, polyethyleneterephthalate (PET) and expanded polytetrafluoroethylene (ePTFE). In particular, ePTFE small caliber vascular grafts are preferred embodiments of the present invention. For purposes of this invention, "vascular grafts" is meant to include endoprostheses.

In another embodiment of the invention, a coating composition is described which includes a polymer backbone to which a reactive functionality is bonded covalently. Although isocyanate functionality is preferred, carboxyl or other reactive functionalities may be substituted for the preferred isocyanate as long as such functionality is reactive with the spacer group as described above.

In this embodiment, at least one pendant moiety is covalently bonded to the reactive functionality (e.g. isocyanate) of the polymer backbone. This pendant moiety is defined by the structure:

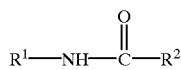

wherein $R^1$ and $R^2$ are a spacer and bio-active agent, respectively, as defined hereinabove.

In a further embodiment of the invention, a method for preparing a bio-active polymer coating is described in which a bio-active agent is covalently bonded through a spacer group to a polymer backbone. As described hereinabove, a reactive functionality such as, for example, an isocyanate functionality is introduced into the polymer backbone. Although the preferred isocyanate functionality is described, any functionality may be used which can participate in covalently bonding a spacer group to the polymer backbone.

Once covalently bonded to the polymer backbone, the reactive functionality is reacted with one end of a hydrophilic spacer having at least one reactive functional group at its first and second ends as described hereinabove. This reaction may be catalyzed by an optional catalyst as described hereinabove. Upon such a reaction, the spacer is attached as a pendant group off of the polymer backbone. By further reacting an unreacted end of the spacer group with a bio-active agent in the presence of an optional catalyst, such as EDC, as described hereinabove, the bio-active agent is covalently bonded to the pendant group.

In yet another embodiment of the invention, there is described a polymer-bound bio-active composition having the following structure:

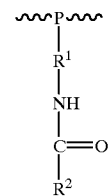

In this structure, as described hereinabove, P, $R^1$, and $R^2$ are a bio-compatible backbone having isocyanate functionality, a spacer group and a bio-active agent, respectively.

In yet another embodiment of the invention, a bio-active coating composition includes a polymer backbone containing reactive functionality, a hydrophilic spacer having at least one functional group at its first and second ends and a bioactive agent which is covalently reactive with the hydrophilic spacer. As used herein, "covalently reactive with" means that the bioactive agent is capable of forming a covalent bond with an unreacted end of the hydrophilic spacer.

In a further embodiment of the invention, a bio-active coating includes a polymer backbone and a bio-active agent bound thereto through a pendant hydrophilic spacer group. This bio-active coating is the reaction product of the chemical combination of a polymer backbone, a hydrophilic spacer and a bio-active agent, all of which are described hereinabove.

The invention being thus described, it will be obvious that the same may be varied in many ways. Such variations are not to be regarded as a departure from the spirit and scope of the invention and all such modifications are intended to be included within the scope of the following claims.

What is claimed is:

1. A biocompatible composition useful as a coating for medical devices, said composition comprising;

a hydrophobic polymer backbone having at least one free reactive functionality independent of any urethane linkages; and a pendant hydrophilic spacer group having a first and second end, said first end bonded to said backbone through said free reactive functionality;

wherein the hydrophilic property of said spacer group and the hydrophobic property of said backbone repel said spacer group away from said backbone to tether said second end of said spacer group at a bio-effective distance from said backbone.

2. The composition of claim 1 wherein said polymer backbone is a polyurethane selected from the group consisting of a segmented poly(esterurethane)urea, a poly(carbonateurethane)urea, a poly(etherurethane)urea, and combinations thereof.

3. The composition of claim 1, wherein said spacer group is selected from the group consisting of aliphatic hydrocarbons, poly(oxy olefins), hydrophilic polyethers, hydrophilic polyethylenes, hydrophilic polyolefins, aliphatic polyesters, polyamines, polysiloxanes, polysilazanes, hydrophilic acrylates, hydrophilic methacrylates, polyamino acids, and linear polysaccharides.

4. The composition of claim 1 further including a bio-active agent covalently bonded to said second end of said spacer group.

5. The composition of claim 4, wherein said bio-active agent is selected from the group consisting of antithrombogenic agents, antibiotics, antibacterial agents, antiviral agents, their pharmaceutical salts and combinations thereof.

6. The composition of claim 4 wherein said bio-active agent is selected from the group of heparin, aldehyde-terminated heparin and pharmaceutical salts thereof.

7. The composition of claim 1, wherein said reactive functionality is selected from the group consisting of isocyanates, carboxyls, amines, and combinations thereof.

8. The composition of claim 1, wherein said spacer group is all amino-terminated poly(ethylene oxide) having a molecular weight of about 100 daltons to about 200,000 daltons.

9. The composition of claim 1, wherein said spacer group is an amino-terminated poly(ethylene oxide) having a molecular weight of about 200 daltons to about 50,000 daltons.

10. The composition of claim 1, wherein said spacer group is an amino-terminated poly(ethylene oxide) having a molecular weight of about 1,000 daltons to about 4,000 daltons.

11. The composition of claim 1, wherein said spacer group has a molecular weight of about 100 daltons to about 200,000 daltons to further define said bio-effective distance.

* * * * *

UNITED STATES PATENT AND TRADEMARK OFFICE
CERTIFICATE OF CORRECTION

PATENT NO. : 6,107,416
DATED : AUGUST 22, 2000
INVENTOR(S) : PATNAIK ET AL.

It is certified that error appears in the above-identified patent and that said Letters Patent is hereby corrected as shown below:

At column 7, line 61, printed patent incorrectely reads "polymer cross-inking", the patent should read -- polymer cross-linking --.

Signed and Sealed this

Twenty-ninth Day of May, 2001

Attest:

NICHOLAS P. GODICI

*Attesting Officer*   Acting Director of the United States Patent and Trademark Office